United States Patent
Jochum

(10) Patent No.: US 9,144,468 B2
(45) Date of Patent: Sep. 29, 2015

(54) FASTENING ELEMENT FOR A PENIS

(76) Inventor: Herbert Jochum, Munsing (DE)

(*) Notice: Subject to any disclaimer, the term of this patent is extended or adjusted under 35 U.S.C. 154(b) by 314 days.

(21) Appl. No.: 13/703,480

(22) PCT Filed: Jun. 14, 2011

(86) PCT No.: PCT/EP2011/059832
§ 371 (c)(1),
(2), (4) Date: Feb. 21, 2013

(87) PCT Pub. No.: WO2011/154556
PCT Pub. Date: Dec. 15, 2011

(65) Prior Publication Data
US 2013/0204081 A1    Aug. 8, 2013

(30) Foreign Application Priority Data
Jun. 11, 2010 (EP) .................................... 10165626

(51) Int. Cl.
| A61F 5/00 | (2006.01) |
| A61B 19/00 | (2006.01) |
| A61F 5/41 | (2006.01) |
| A61B 17/326 | (2006.01) |

(52) U.S. Cl.
CPC ............... *A61B 19/24* (2013.01); *A61B 17/326* (2013.01); *A61F 5/41* (2013.01)

(58) Field of Classification Search
CPC ......................................................... A61F 5/41
USPC .......................................................... 600/38–41
See application file for complete search history.

(56) References Cited

U.S. PATENT DOCUMENTS

| 5,924,567 A * | 7/1999 | Wenum .................. 206/362.3 |
| 8,075,473 B2 * | 12/2011 | Rudi ........................... 600/38 |
| 2007/0181455 A1 * | 8/2007 | Davis ....................... 206/362.3 |

FOREIGN PATENT DOCUMENTS

| DE | 92 10 914.4 U1 | 1/1993 |
| DE | 20 2006 017 667 U1 | 4/2007 |
| DE | 10 2007 020 236 B3 | 4/2008 |

OTHER PUBLICATIONS

Written Opinion for PCT/EP2011/059832, Oct. 12, 2011.
International Search Report for PCT/EP2011/059832, Oct. 12, 2011.

* cited by examiner

*Primary Examiner* — John Lacyk
(74) *Attorney, Agent, or Firm* — Bacon & Thomas, PLLC

(57) ABSTRACT

A fastening element for a penis enabling connecting to a penis extension device provided with a supporting element as well as a fixing element for the penis, the supporting element being connected to a cover so as to be movable, the cover being moveable between an open and a closed position, and when the cover is in the closed position, the supporting element together with the cover forms a tubular hollow body having a proximal end and a distal end.

11 Claims, 4 Drawing Sheets

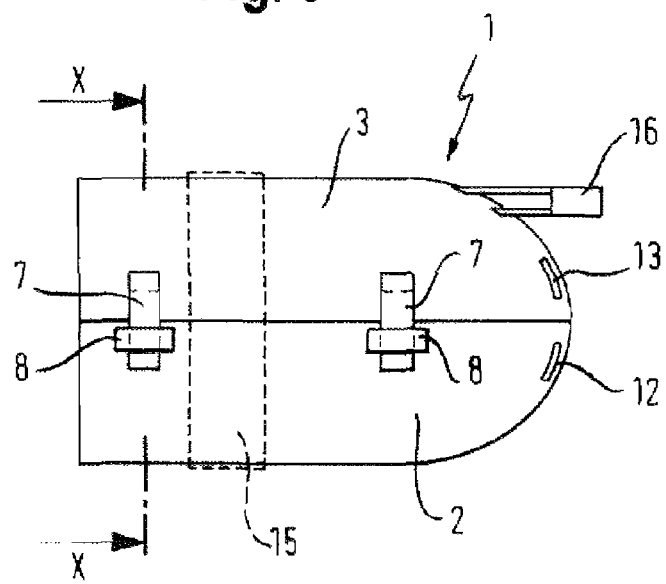
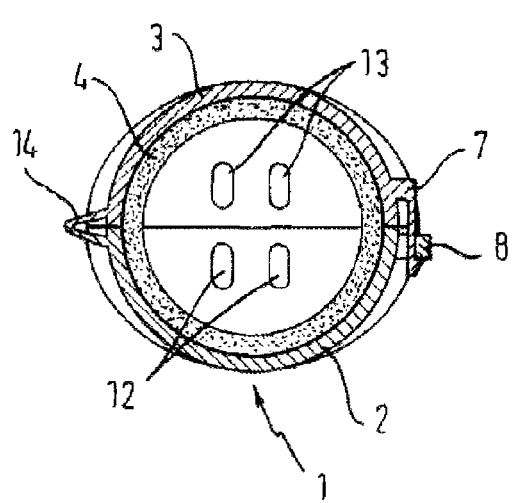
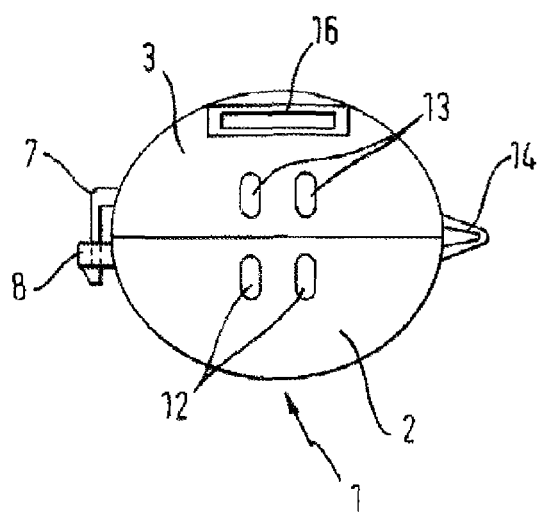

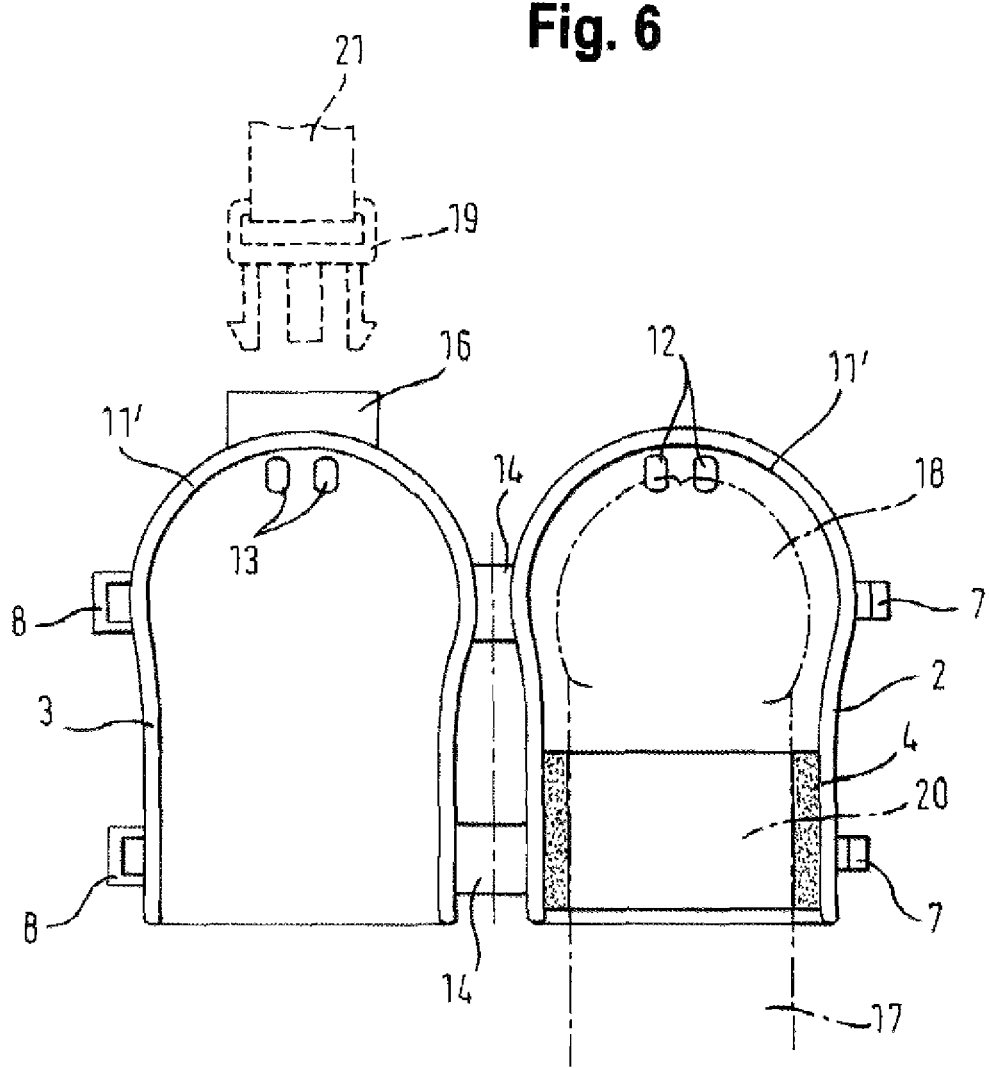

FASTENING ELEMENT FOR A PENIS

BACKGROUND OF THE INVENTION

A. Field of the Invention

The invention relates to a fastening element for a penis for connecting to a penis extension device which is provided with a supporting element as well as a fixing element for the penis.

B. Related Art

Numerous diverse configurations of penis extension devices or means are known, cf. for example DE 100 01 331 A1, U.S. Pat. No. 5,707,341 and EP 1 779 822 A1.

What these devices have in common is that a longer-acting traction is exerted on the penis so that new tissue is formed and results in an enlargement of the penis. Various diseases can be treated using these devices. Hence, the present invention does not relate to erection aids or the like. On the contrary, traction is exerted on the penis in the non-erect state.

For this purpose, the penis extension device is required to be connected to the penis so as to be able to exert said traction. It goes without saying that the starting point for transmitting traction should be at the distal end of the penis.

Using a loop engaging behind the glans of the penis to connect a penis extension device to the penis is currently proposed. Condoms and cylindrical hollow bodies have furthermore been proposed (U.S. Pat. No. 5,707,341 and EP 1 779 822 A1).

So-called glans cradles are known from DE 20 206 017 667 U1 and DE 20 207 003 824 U1, onto which the penis is placed and fixed by means of a fixing element. The fixing element engages behind the glans, and hence at the proximal side of the glans, and prevents the penis from being pulled away from the supporting element when a traction is exerted.

A disadvantage of these known fastening elements is that either they do not reliably fix the penis or are made of several parts and are complicated to put on.

A task of the invention is to provide a simply constructed generic fastening element which is of simple construction and guarantees a reliable as well as protective connection to the penis extension device.

SUMMARY OF THE INVENTION

This task is solved by a fastening element according to the invention.

A supporting element is hereby meant as such an element onto which the penis is placed and which localizes the penis so as to be stationary by means of the fixing element.

The fastening element according to the invention is characterized in that the supporting element is movably connected to a cover. This cover can assume a closed position in which, together with the supporting element, it forms a tubular hollow body in which the penis comes to rest. This tubular hollow body thus has a proximal end facing the body and a distal end facing away from the body. The penis hence lies within this hollow body.

The cover is not only able to assume a closed position but also an open position. Within the framework of the present documents, an open position is not identified as a specific position. It should rather be hereby expressed that the cover can be brought from the closed position into another position where the cover and supporting element no longer form a "closed tube" together.

The tubular hollow body can incidentally be of any arbitrary cross section. In the simplest case, the supporting element constitutes a planar strip which will be closed by a rectangular or circular cover so as to yield an overall hollow body of rectangular cross section. Ideally, however, the cross section of the hollow body is round or oval. In other words, the hollow body represents a tube having the corresponding cross section.

The supporting element and the cover preferably each form a tubular half shell. It is in this case not imperative for the two parts to form a complete half shell and thus half of a tube. On the contrary, the supporting element, for instance, can form a shell which represents only a certain fraction of the full tube when the supporting element and the cover are assembled. Preferably, the two half shells are approximately cylindrical half shells of about the same size.

The connection between the cover and the supporting element can be of any arbitrary kind, for example hinges, joints or the like. Preferably, the two half shells of supporting element and cover are connected to each other on one of their longitudinal sides so as to be movable. In other words, two longitudinal sides of the half shell abutting against each other in the closed state are movably connected to one another.

On the two other longitudinal sides, the two half shells are preferably provided with closing means which, on the one hand, enable the two half shells to be permanently connected to each other and, on the other, the connection to be released so that the supporting element and the cover can be "folded open." These closing means can be usual ones. They can thus be a clip or snap-in connection, for example.

The tubular hollow body formed by the supporting element and the cover is preferably closed at its distal end. The supporting element and/or the cover is/are provided with at least one opening at said closed distal end. In other words, both the supporting element and the cover can have an opening at its distal end.

According to a further preferred embodiment, the tubular hollow body is closed at its distal end while forming a dome. This dome is preferably wider than the tubular hollow body. Appropriately, the glans comes to rest within this dome.

The supporting element and the cover are preferably manufactured of a dimensionally stable plastic material. The elements which allow the connection of the supporting element and the cover to be movable are preferably integrally formed with same. The same applies to the closing means.

The supporting element and/or the cover can also be manufactured of a rubber or a rubber-like material. However, said material must have such a hardness and/or wall thickness that, even during tensile stress, the hollow body is of such a dimensional stability that the penis situated within the hollow body is not "squeezed." It is also possible for the supporting element to be manufactured of a dimensionally stable plastic material and the cover of a rubber or rubber like material such as described above. The same applies vice versa. All that needs to be ensured is that the tubular shape, respectively the tubular hollow body shape, will be more or less maintained and the available space for the penis is not unnecessarily restricted or reduced.

Using the fastening element according to the invention, it is possible to connect the penis to the associated penis extension device in a reliable and long-term manner and to exert a traction. Furthermore, the penis will be protected since it is completely enclosed by the tubular hollow body. Under tensile load, the penis can thus not rub against underwear or the like so that irritations are avoided. This applies particularly to uncircumcised males where the foreskin has to be pulled back so that the fixing element can engage on the proximal side of the glans so as to fulfill its function.

To be able to exert a traction on the fastening element by means of the penis extension device, either the supporting element or the cover is preferably provided with a connecting element at its distal end which will be connected to the extension device.

The fixing element of the fastening element according to the invention is preferably situated at the proximal end or close to the proximal end of the fastening element.

BRIEF DESCRIPTION OF THE DRAWINGS

The invention will be explained hereinafter on the basis of the accompanying drawings which are not to scale and are sketches. These drawings show.

DETAILED DESCRIPTION OF VARIOUS EMBODIMENTS OF THE INVENTION

Figure 1:
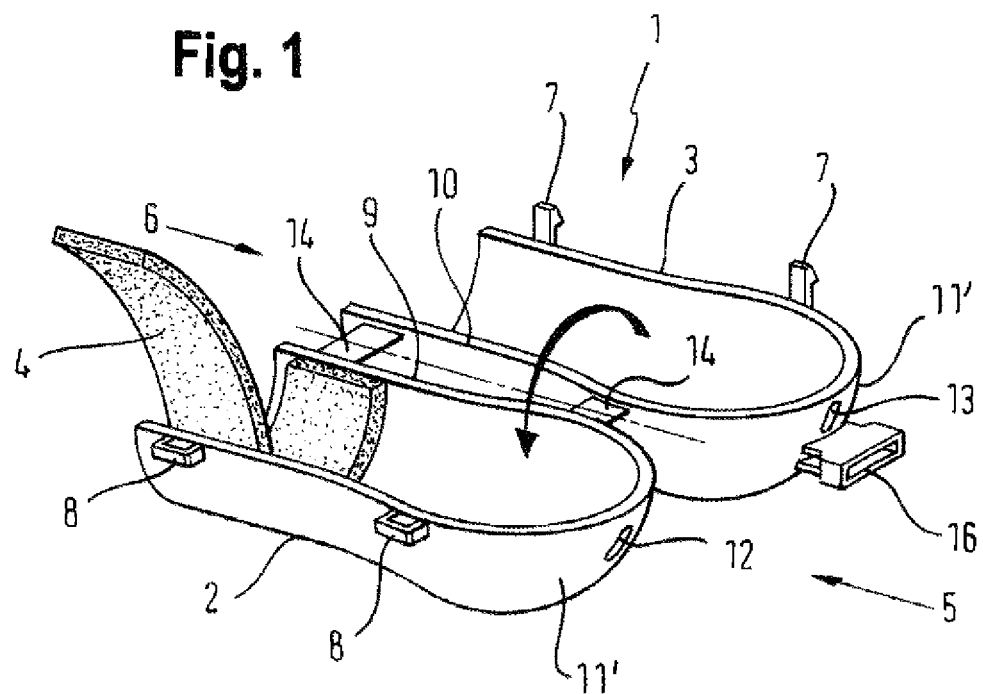
FIG. 1 a perspective view of a fastening element according to the invention in an open position, FIG. 2 a perspective view of the fastening element shown in FIG. 1 in the closed position, FIG. 3 a side view of the fastening element shown in FIG. 2, FIG. 4 a cross-sectional view of the fastening element shown in FIG. 3 along line X-X, FIG. 5 a frontal view of the fastening element shown in FIG. 3, and hence a view from the right side relative FIG. 3, FIG. 6 a top view from above of the fastening element shown in FIG. 1 in an open position with a penis inserted, and FIG. 7 a frontal view of a person wearing a penis extension device which exerts a traction on the penis by means of the fastening element according to the invention.

The fastening element 1 shown in FIG. 1 in a perspective view comprises a supporting element 2 and a cover 3 which are movably connected to one another by means of two hinges 14. These hinges 14 engage close to or at the longitudinal side 10 opposite the cover 3 and the longitudinal side 9 of the supporting element 2.

Figure 2:
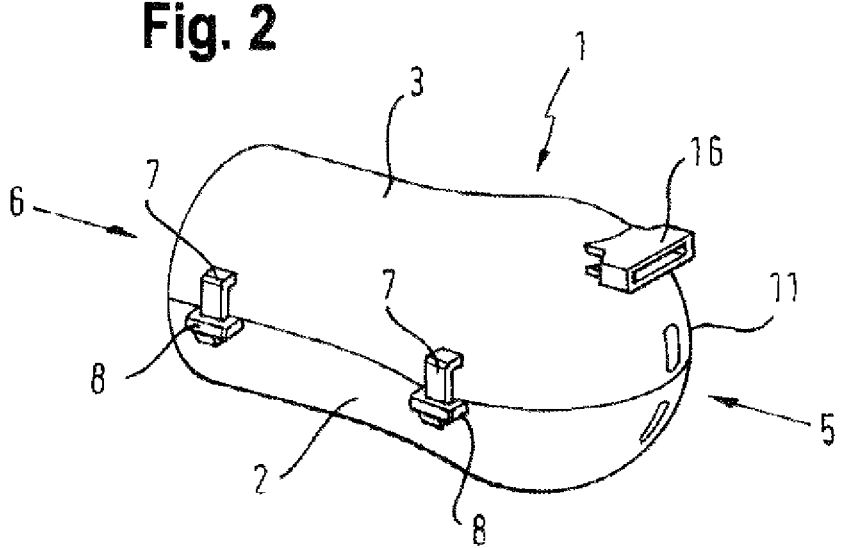

In order to attain the closed position shown in FIG. 2, the cover 3 is pivoted pursuant the arrow shown in FIG. 1 so that the cover 3 comes to rest on the supporting element 2 and forms a tubular hollow body 2, 3. This tubular hollow body is illustrated in FIG. 2 in a perspective view and has a distal end 5 and a proximal end 6.

The supporting element 2 and the cover 3 represent two half shells of approximately the same size forming a "half" dome 11' at the distal end 5 which together form a "full" dome 11 when in the closed position shown in FIG. 2.

The tubular hollow body 2, 3 is thus shut at said distal end 5 by dome 11.

The tubular hollow body 2, 3 is wider in this dome area than the remaining area of the hollow body 2, 3. In other words, the diameter of the hollow body 2, 3 increases from the proximal side and, after reaching a maximum relative the proximal end, then decreases so as to form the mentioned dome 11.

Incidentally, it is not imperative for the hollow body 2, 3 to be closed at the proximal end 5 in the described manner and way. It can also be open at said proximal end 6. Any desired size can be selected for the opening. In the simplest case, the hollow body 2, 3 can be formed of a tubular section having a constant or else varying diameter.

At the proximal end 6, a fixing element in the form of a strip 4 of an elastic material is inserted which is appropriately connected to the supporting element 2, e.g. by gluing.

Both the cover 3 and the supporting element 2 have two respective openings 12 and 13 at their respective distal end 5, also cf. FIGS. 4 and 5.

To keep the cover 3 and the supporting element 2 in the closed position, hooks 7 are provided on the cover 3 which engage and snap into eyelets 8 on the supporting element 2. These hooks 7 and eyelets 8 are arranged on the longitudinal sides of cover 3 and supporting element 2 opposite the longitudinal sides 9, respectively 10.

The fastening element 1 shown in the figures is made of a plastic material, e.g. injection-molded. The hinges 14 can be film hinges. These film hinges 14 as well as the hooks 7 and eyelets 8 are integrally injection-molded with the cover 3, respectively supporting element 2. In addition, the fastening element is a dimensionally stable element which keeps or only slightly changes its shape when a force or traction usual for penis extension devices is exerted.

Instead of the hooks 7 and eyelets 8, a Velcro strap 15 can be employed which will be wrapped around the fastening element 1 when in the closed position. Reference is made in this respect to FIG. 3.

At its distal end 5, the cover 3 is provided with the female part 16 of a quick release fastener or click buckle which is molded on the cover 3.

To connect the fastening element 1 to the penis 17, the latter 17 is brought into a horizontal position pointing away from the body and placed on or inserted into the supporting element 2 (cf. FIG. 6). In doing so, the glans 18 comes to rest in the half dome 11'.

As can be seen from FIG. 6, the fixing element 4 is then situated on the proximal side of glans 18.

Subsequently, the cover 3 is pivoted over the supporting element 2 so that the hollow body 2, 3 is shut. In this case, care has to be taken that the fixing element 4 runs around the penis shaft 20 in order to fix same centrically within the hollow body 2, 3 so that the penis cannot be pulled out even when traction is applied.

To apply said traction to the fastening element 1, the penis 17 together with the fastening element 1 is eased back towards the body against the abdomen. The male part 19 of the quick release fastener corresponding to the female part 16 of said quick release fastener is introduced into said female part 16. The male part 19 is additionally connected to a strap.

Figure 7:
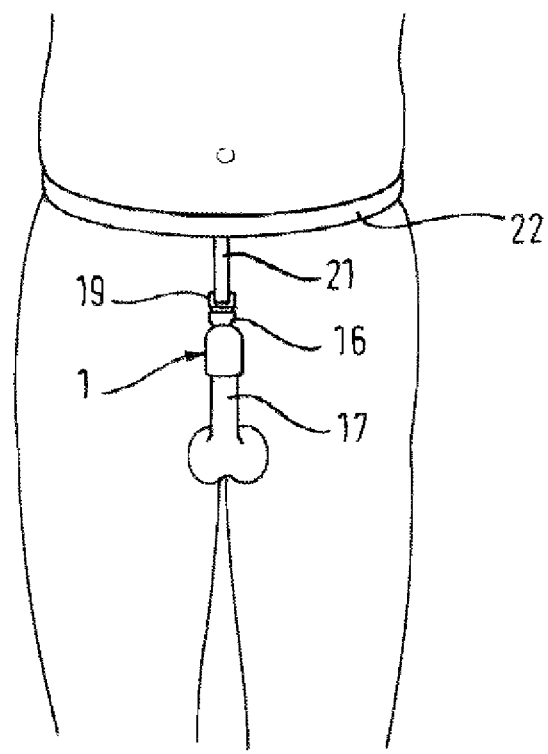

FIG. 7 shows how this strap 21 is connected to a belt 22 or the like which runs around the abdominal area of a person. Either the strap 21 or the belt 22 or else both 21, 22 is/are made of an elastic material. Strap 21 and/or belt 22 are tightened so that the fastening element 1 exerts a pulling action on the penis 17.

LIST OF REFERENCE NUMERALS 1 fastening element
2 supporting element
3 cover
4 fixing element
5 distal end
6 proximal end
7 hook
8 eyelet
9 longitudinal side of supporting element 2
10 longitudinal side of cover 3
11 dome
11' half dome
12 opening
13 opening
14 hinge
15 Velcro strap
16 female part of quick release fastener/click buckle
17 penis 18 glans
19 male part of quick release fastener/click buckle
20 penis shaft
21 strap
22 belt

The invention claimed is:

1. A fastening element adapted to connect a penis to a penis extension device comprising:
   a supporting element connected to a moveable cover, the cover moveable between an open and a closed position,
   the supporting element together with the cover in the closed position forming a tubular hollow body having a proximal end and a distal end,
   wherein either the supporting element or the cover has a connecting element adapted to connect to a penis extension device at the distal end.

2. The fastening element according to claim 1, wherein the supporting element and the cover each form a tubular half shell, and, when the cover is in the closed position, the two half shells define a full tube forming the hollow body.

3. The fastening element according to claim 1, wherein the two half shells are approximately cylindrical half shells.

4. The fastening element according to claim 3, wherein the two half shells have opposed longitudinal sides and are movably connected to one another along one of their longitudinal sides.

5. The fastening element according to claim 1, wherein the tubular hollow body is closed at its distal end.

6. The fastening element according to claim 5, wherein either or both the supporting element and the cover is provided with at least one respective opening at the distal end.

7. The fastening element according to claim 6, wherein the tubular hollow body is shut at the distal end and is dome shaped at the distal end.

8. The fastening element according to claim 7, wherein the dome shape is wider than the tubular hollow body.

9. The fastening element according to claim 1, wherein the supporting element and the cover are made from a dimensionally stable plastic material or a flexible material.

10. The fastening element according to claim 1, comprising a penis fixing element arranged at or close to the proximal end.

11. The fastening element according to claim 4, wherein the two half shells are provided with a closure on their opposite longitudinal side, which closure, on the one hand, enables the two half shells to be permanently connected to each other and, on the other hand, the connection to be released.

* * * * *